United States Patent
Claus

(10) Patent No.: US 10,080,681 B2
(45) Date of Patent: *Sep. 25, 2018

(54) CONTROLLING A PHACOEMULSIFICATION SYSTEM BASED ON REAL-TIME ANALYSIS OF IMAGE DATA

(71) Applicant: ABBOTT MEDICAL OPTICS INC., Santa Ana, CA (US)

(72) Inventor: Michael J. Claus, Lakewood Ranch, FL (US)

(73) Assignee: Johnson & Johnson Surgical Vision, Inc., Santa Ana, CA (US)

(*) Notice: Subject to any disclaimer, the term of this patent is extended or adjusted under 35 U.S.C. 154(b) by 16 days.

This patent is subject to a terminal disclaimer.

(21) Appl. No.: 15/256,420

(22) Filed: Sep. 2, 2016

(65) Prior Publication Data

US 2016/0367401 A1 Dec. 22, 2016

Related U.S. Application Data

(62) Division of application No. 14/147,213, filed on Jan. 3, 2014, now Pat. No. 9,433,472, which is a division of application No. 12/135,734, filed on Jun. 9, 2008, now Pat. No. 8,622,951.

(51) Int. Cl.
| | | |
|---|---|---|
| *A61F 9/007* | (2006.01) | |
| *A61F 9/008* | (2006.01) | |
| *A61B 90/00* | (2016.01) | |
| *A61B 90/20* | (2016.01) | |
| *A61B 17/00* | (2006.01) | |
| *A61B 17/02* | (2006.01) | |
| *A61B 34/00* | (2016.01) | |
| *A61B 34/10* | (2016.01) | |

(52) U.S. Cl.
CPC .......... *A61F 9/00745* (2013.01); *A61B 90/20* (2016.02); *A61B 90/361* (2016.02); *A61B 17/0231* (2013.01); *A61B 34/10* (2016.02); *A61B 2017/00057* (2013.01); *A61B 2017/00115* (2013.01); *A61B 2034/254* (2016.02); *A61B 2090/3612* (2016.02)

(58) Field of Classification Search
None
See application file for complete search history.

(56) References Cited

U.S. PATENT DOCUMENTS

| | | |
|---|---|---|
| 5,078,140 A | 1/1992 | Kwoh |
| 6,155,975 A | 12/2000 | Urich et al. |
| 6,311,540 B1 | 11/2001 | Paltieli et al. |
| 7,040,759 B2 | 5/2006 | Chernyak et al. |
| 7,044,602 B2 | 5/2006 | Chernyak |
| 7,135,016 B1 * | 11/2006 | Asia ........................ A61F 9/008 606/12 |
| 7,261,415 B2 | 8/2007 | Chernyak |
| 8,982,195 B2 | 3/2015 | Claus et al. |
| 2003/0036751 A1 | 2/2003 | Anderson et al. |
| 2003/0083536 A1 | 5/2003 | Eshel et al. |
| 2003/0159141 A1 | 8/2003 | Zacharias |
| 2004/0146201 A1 | 7/2004 | Sathyanarayana |
| 2004/0152990 A1 | 8/2004 | Mackool |
| 2004/0267136 A1 * | 12/2004 | Yaguchi .............. A61F 9/00745 600/459 |
| 2005/0261628 A1 | 11/2005 | Boukhny et al. |
| 2006/0159319 A1 | 7/2006 | Sathyanarayana |
| 2008/0058782 A1 | 3/2008 | Frangineas et al. |
| 2008/0110236 A1 | 5/2008 | Hajishah et al. |

FOREIGN PATENT DOCUMENTS

CA 2662869 A 3/2008

OTHER PUBLICATIONS

International Search Report and Written Opinion, dated Sep. 23, 2009, and International Preliminary Report on Patentability, dated Dec. 13, 2010, for Application No. PCT/US2009/046368, 9 pages.

* cited by examiner

*Primary Examiner* — H. Sarah Park
(74) *Attorney, Agent, or Firm* — Johnson & Johnson Surgical Vision, Inc.

(57) ABSTRACT

A design for dynamically adjusting parameters applied to a surgical instrument, such as an ocular surgical instrument, is presented. The method includes detecting surgical events from image data collected by a surgical microscope focused on an ocular surgical procedure, establishing a desired response for each detected surgical event, delivering the desired response to the ocular surgical instrument as a set of software instructions, and altering the surgical procedure based on the desired response received as the set of software instructions.

7 Claims, 6 Drawing Sheets ns and
subsystems. Another system related to capturing of optical
images, specifically eye position, is reflected in the U.S. Pat.
No. 7,044,602 to Chernyak, U.S. Pat. No. 7,261,415 to
Chernyak, and U.S. Pat. No. 7,040,759 to Chernyak et al.,
each assigned to VISX, Incorporated of Santa Clara, Calif.

CONTROLLING A PHACOEMULSIFICATION SYSTEM BASED ON REAL-TIME ANALYSIS OF IMAGE DATA

This application claims priority to and is a divisional of U.S. application Ser. No. 14/147,213, filed Jan. 3, 2014, which is a divisional application and claims priority to U.S. application Ser. No. 12/135,734, entitled "Controlling a Phacoemulsification System Based on Real-Time Analysis of Image Data", filed on Jun. 9, 2008, the entire contents of which are hereby incorporated by reference in their entirety for all purposes as if fully set forth herein.

BACKGROUND OF THE INVENTION

Field of the Invention

The present invention relates generally to the field of ocular surgery, and more specifically to real-time control of a medical instrument system during ophthalmic procedures based on detected surgical events.

Description of the Related Art

Ocular surgery, such as phacoemulsification surgery, requires a surgeon to continuously make decisions while conducting the surgical procedure. To make these decisions, the surgeon may rely on a variety of information originating within the surgical theater environment, which may include the surgeon using her auditory, tactile, and visual senses to ascertain cues during the procedure. The surgeon may use these environmental cues to make decisions regarding adjusting and refining the settings and parameters controlling the medical instrument system to best perform the most effective, efficient and safest possible surgical procedure. One example of an environmental cue is reporting an audible alarm to inform the surgeon that the instrument logic has detected a parameter, such as flow for example, has reached a value outside of a desired operating range.

Medical instrument systems incorporate numerous sensors to detect and collect information from the surgical theater environment sensors and provide this information as input to software programs that monitor the medical instrument system. Together with advancements in sensor technologies, surgical monitoring software programs continue to evolve to take advantage of advanced sensor capabilities. One example of the current state of software sensor state of the art is Advanced Medical Optics' "occlusion mode" functionality provided in certain phacoemulsification systems, wherein a control program monitors vacuum sensors and recognizes vacuum levels exceeding a particular value. Once the control program detects that vacuum levels have exceeded the value, the control program adjusts system parameters accordingly.

The current state of the art also entails capturing optical images during the surgical procedure and presenting these optical images with the various instrument settings and sensor readings. One example of such a design is Advanced Medical Optics' "Surgical Media Center," aspects of which are reflected in U.S. patent application Ser. No. 11/953,229, "DIGITAL VIDEO CAPTURE SYSTEM AND METHOD WITH CUSTOMIZABLE GRAPHICAL OVERLAY," inventors Wayne Wong, et al., filed Dec. 10, 2007 (issued as U.S. Pat. No. 8,982,195 on Mar. 17, 2015), the entirety of which is incorporated herein by reference. The Surgical Media Center provides simultaneous replay of surgical camera video images synchronized with medical instrument system settings and parameters. Video and system settings information can be communicated to other systems and subsystems. Another system related to capturing of optical images, specifically eye position, is reflected in the U.S. Pat. No. 7,044,602 to Chernyak, U.S. Pat. No. 7,261,415 to Chernyak, and U.S. Pat. No. 7,040,759 to Chernyak et al., each assigned to VISX, Incorporated of Santa Clara, Calif.

Phacoemulsification instrument systems manufacturers provide products that allow the sensors within the systems to detect information from the surgical environment and pass that data to control programs in order to dynamically generate responses and adjust instrument system settings. In conjunction, manufacturers continue to evolve and improve data analysis programs to recognize certain patterns of information reported from digital video camera imaging data. Image analysis techniques may afford the system the ability to perceive small changes or complex patterns otherwise undetected by a surgeon operating a surgical microscope. Important visual information or cues previously unavailable during a surgical procedure can now be employed during the procedure.

Ocular surgical procedures in particular, including phacoemulsification, involve manual procedures selected by the surgeon based on environmental cues originating from instrument sensors. While manual procedures are effective and in wide use, current surgical procedures can be challenging in a surgical environment due to human response time and the ability to perceive very small changes or very complex patterns within environmental cues. It can be difficult for the surgeon to observe available environmental cues, and appropriately respond to these 'events' quickly and accurately by determining and manually implementing new settings and parameters to adjust the surgical instrument. Enhancing a surgeon's ability to perform the surgical procedure is always advantageous.

Based on the foregoing, it would be advantageous to provide for a system and method that enhances the ability of the system to accurately detect, report, and quickly respond to surgical events from imaging data, and provide information relating environmental changes previously not perceived by the surgeon for use in medical instrument systems that overcomes drawbacks present in previously known designs.

SUMMARY OF THE INVENTION

According to one aspect of the present design, there is provided an apparatus configured to control parameters of a surgical instrument employable in a surgical procedure, such as an ocular surgical procedure. The apparatus comprises an image analysis module configured to detect surgical events within an image data stream and an instrument control module configured to receive surgical events detected from at least the image analysis module and generate responses to said detected surgical events. The instrument control module is configured to process said responses and transmit processed responses in the form of an instruction set. The surgical instrument is configured to receive and execute instruction sets communicated from the instrument control module during the surgical procedure.

According to another aspect of the present design, there is provided a method for dynamically adjusting parameters applied to a surgical instrument, such as an ocular surgical instrument. The method includes detecting surgical events from image data collected by a surgical microscope focused on an ocular surgical procedure, establishing a desired response for each detected surgical event, delivering the desired response to the ocular surgical instrument as a set of software instructions, and altering the surgical procedure based on the desired response received as the set of software instructions.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

Figure 1:
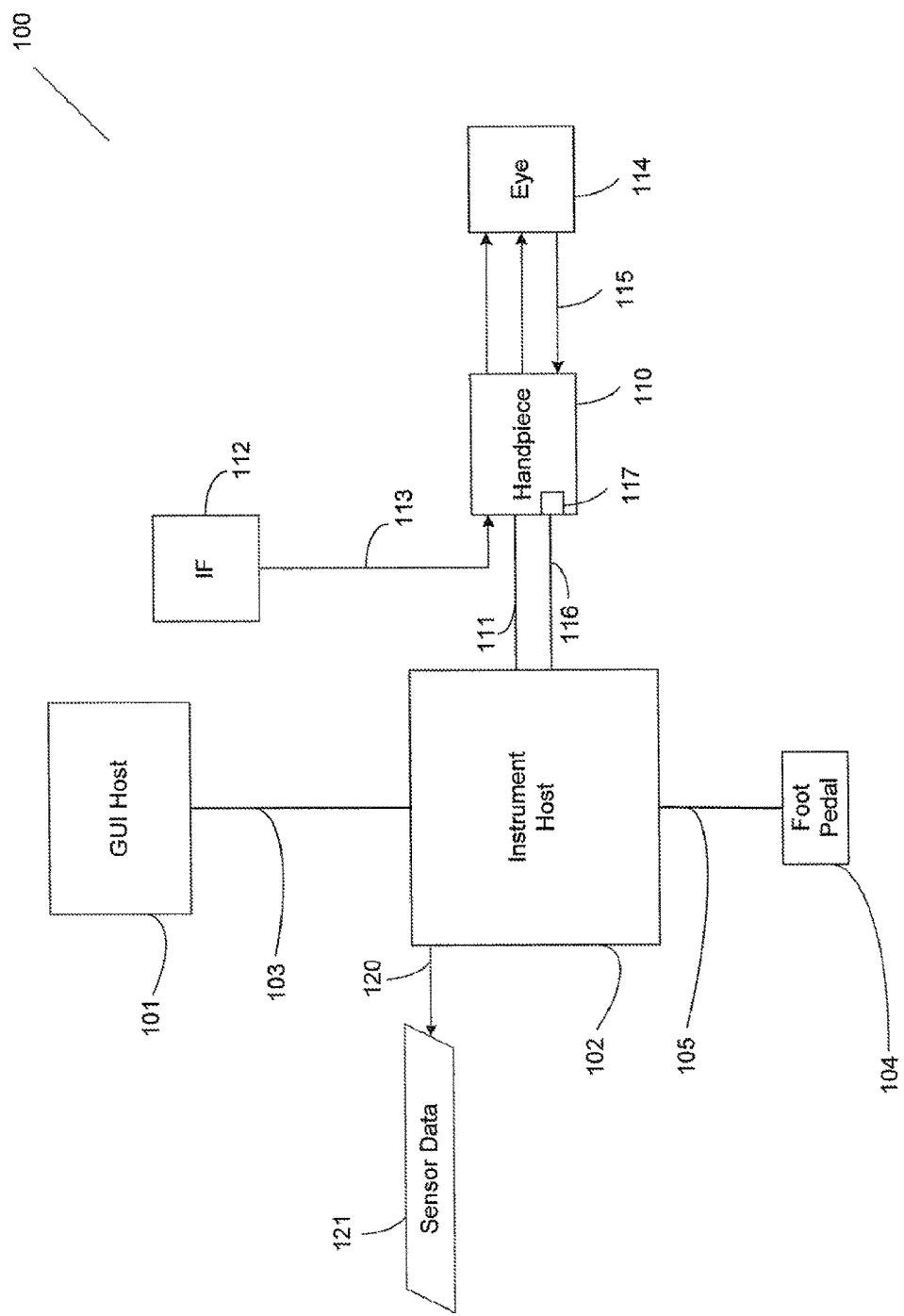
FIG. 1 illustrates an exemplary phacoemulsification/vitrectomy system in a functional block diagram to show the components and interfaces for a safety critical medical instrument system that may be employed in accordance with an aspect of the present invention.

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to mechanized control for adjusting surgical instrument settings and/or parameters, e.g. vacuum, aspiration, etc., based on detected surgical events originating within the surgical operating theater environment. The present design arrangement may include an image analysis component configured to recognize and report surgical events determined from the imaging data, such as imaging data received from a camera or via a surgical microscope. The arrangement typically includes an instrument sensor monitoring and analysis component configured to recognize and report surgical events determined from instrument sensor data. In addition, the arrangement may include a surgical instrument controller configured to generate and transmit responses instructing the surgical instrument to adjust specific settings and/or parameters and alter the course of the remaining surgery. The present design thus provides for dynamic or real-time control of the medical instrument system and/or medical or surgical instrument.

In short, the present design provides for real-time control of the medical instrument system, affording alterations to the course of the remaining surgical procedure, realized from real-time analysis of video imaging data. Analysis of the imaging data is typically automated or automatic, i.e. requires zero or minimal user interface. Analysis of instrument sensor data may be employed separately or in combination with image data processing to detect surgical events.

Any type of system or software application configured to receive detected events from imaging and sensor data analysis, for example a pilotless flight control application, may benefit from the design presented herein, and such a design is not limited to a phacoemulsification system, surgical system, or even a medical system. The present design may be implemented in, for example, systems including but not limited to phacoemulsification-vitrectomy systems, vitrectomy systems, dental systems, industrial applications, and aerospace applications.

The present design may include a graphical user interface to further control automated operations and may include configuration and setup functionality. The system can provide the ability to assign various predetermined settings and parameters in response to specific detected surgical events and show video and instrument sensor data.

The present design is intended to provide a reliable, noninvasive, and efficient automatic control mechanism for a medical instrument system for use in dynamically controlling the surgical instrument system in real-time.

System Example

While the present design may be used in various environments and applications, it will be discussed herein with a particular emphasis on a medical or hospital environment, where a surgeon or health care practitioner performs. For example, one embodiment of the present design is in or with a phacoemulsification surgical system that comprises an independent graphical user interface (GUI) host module, an instrument host module, a GUI device, and a controller module, such as a foot switch, to control the surgical system.

FIG. 1 illustrates an exemplary phacoemulsification/vitrectomy system 100 in a functional block diagram to show the components and interfaces for a safety critical medical instrument system that may be employed in accordance with an aspect of the present invention. A serial communication cable 103 connects GUI host 101 module and instrument host 102 module for the purposes of controlling the surgical instrument host 102 by the GUI host 101. Instrument host 102 may be considered a computational device in the arrangement shown, but other arrangements are possible. An interface communications cable 120 is connected to instrument host 102 module for distributing instrument sensor data 121, and may include distribution of instrument settings and parameters information, to other systems, subsystems and modules within and external to instrument host 102 module. Although shown connected to the instrument host 102 module, interface communications cable 120 may be connected or realized on any other subsystem (not shown) that could accommodate such an interface device able to distribute the respective data.

A switch module associated with foot pedal 104 may transmit control signals relating internal physical and virtual switch position information as input to the instrument host 102 over serial communications cable 105. Instrument host 102 may provide a database file system for storing configuration parameter values, programs, and other data saved in a storage device (not shown). In addition, the database file system may be realized on the GUI host 101 or any other subsystem (not shown) that could accommodate such a file system.

The phacoemulsification/vitrectomy system 100 has a handpiece 110 that includes a needle and electrical means, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to a patient's eye, or affected area or region, indicated diagrammatically by block 114. Alternatively, the irrigation source may be routed to eye 114 through a separate pathway independent of the handpiece. Aspiration is provided to eye 114 by the instrument host 102 pump (not shown), such as a peristaltic pump, through lines 115 and 116. A switch 117 disposed on handpiece 110 may be utilized to enable a surgeon/operator to select an amplitude of electrical pulses to the handpiece via the instrument host and GUI host. Any suitable input device, such as for example, a foot pedal 104 switch may be utilized in lieu of switch 117.

In combination with phacoemulsification system 100, the present design surgical system includes image processing in or with the phacoemulsification system and may comprise a surgical microscope, digital video cameras, data storage, video rendering, and user interface to control the image capture and analysis system.

Figure 2:
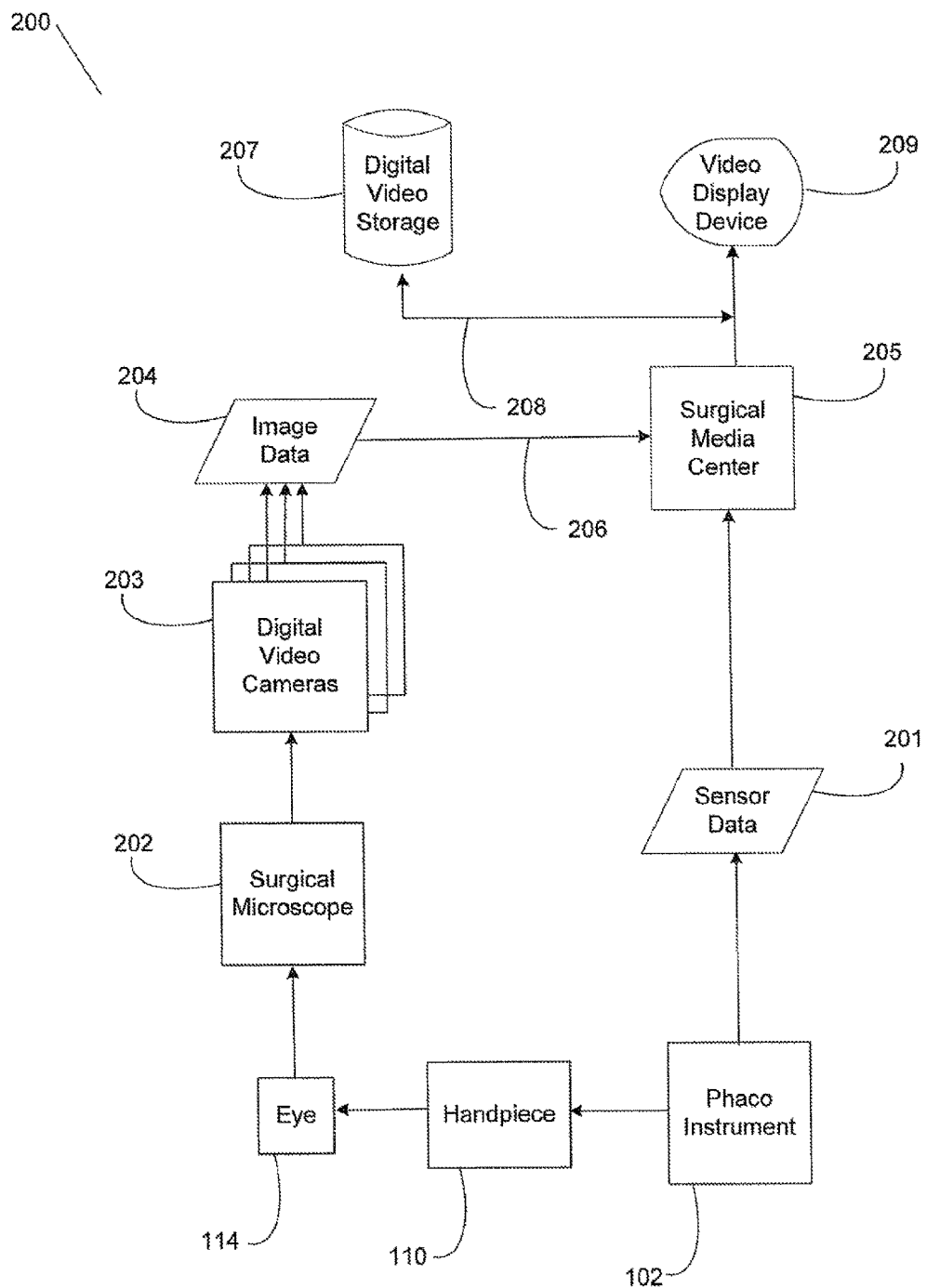
FIG. 2 illustrates an exemplary surgical system in a functional block diagram to show the components and interfaces for a real-time digital image capture and presentation system that may be employed in accordance with an aspect of the present invention.

FIG. 2 illustrates an exemplary surgical system 200 in a functional block diagram to show the components and interfaces for a real-time digital image capture, distribution, and presentation system that may be employed in accordance with an aspect of the present invention. The surgical system digital image processing design will be discussed herein based on Advanced Medical Optic's surgical media center features and functionality.

Surgical system 200 may include a surgical instrument, for example phacoemulsification instrument 102, such as the phacoemulsification/vitrectomy system 100 shown in FIG. 1. Surgical system 200 may further include a surgical microscope 202 focused on the surgical procedure, e.g. patients eye, and may involve digital video cameras 203, or other device suitable for video recording, and may transfer the resulting image data at 204, in analog or digital form, to surgical media center 205 via communications cable 206. Surgical media center 205 is a processing device that manages the multimedia data recorded by the surgical microscope, and the instrument sensor data 121 in real-time, including but not limited to vacuum, power, flow, and foot pedal position generated from phacoemulsification instrument 102 during the surgical procedure. Managing the multimedia data includes synchronizing the temporal relationship between the instrument parameters, settings, and sensor data from phaco instrument 102 and the optical data from surgical microscope 202. In this arrangement, system 200 may communicate the digital video as an image data stream, representing the optical data from the procedure/surgery, with the medical system instrument parameters, settings, and sensor data reported by phaco instrument 102 in real-time to other systems and subsystems.

The surgical media center may further include a digital video storage device 207 configured to store the multimedia data recorded. Video storage device 207 may connect to and be accessed by surgical media center 205 via communications cable 208. In addition, a video display device 209 may connect to surgical media center 205 and digital video storage device 207 via communications cable 208.

In this configuration, surgical media center 205 may record and present a video image of the procedure/surgery with the medical system instrument parameters and settings utilized by the phacoemulsification instrument 102 in real-time. Surgical media center 205 may synchronize instrument data with the video stream allowing simultaneous display of video data with a graphical overlay showing the corresponding parameters and system settings at each instant of the procedure on a frame-by-frame basis. This cumulative data, i.e. the video data synchronized with the setting and parameter data may be stored and archived in digital video storage device 207. During playback, the user may select to show or hide different elements of the instrument data rendered on video display device 209.

Event Detection and Instrument Control

The present design typically includes a real-time surgical instrument control module configured to receive detected surgical events and dynamically adjust instrument parameters and settings to alter the course of the remaining surgery. Detected surgical events may originate from image analysis software, instrument sensor monitoring software, and other software components configured to analyze information collected from the surgical environment. The detected surgical events, including but not limited to commencements of procedures, termination of procedures, changes in system or patient parameters such as pressure applied, pressure available, patient blood pressure, patient temperature, instrument temperature, and so forth, may be electronically communicated to the instrument control module for matching an appropriate response to received events and sending the response(s) to the surgical instrument. The response may include commands or instructions containing information relaying adjustments or changes to in-effect instrument settings and parameters.

System

Figure 3:
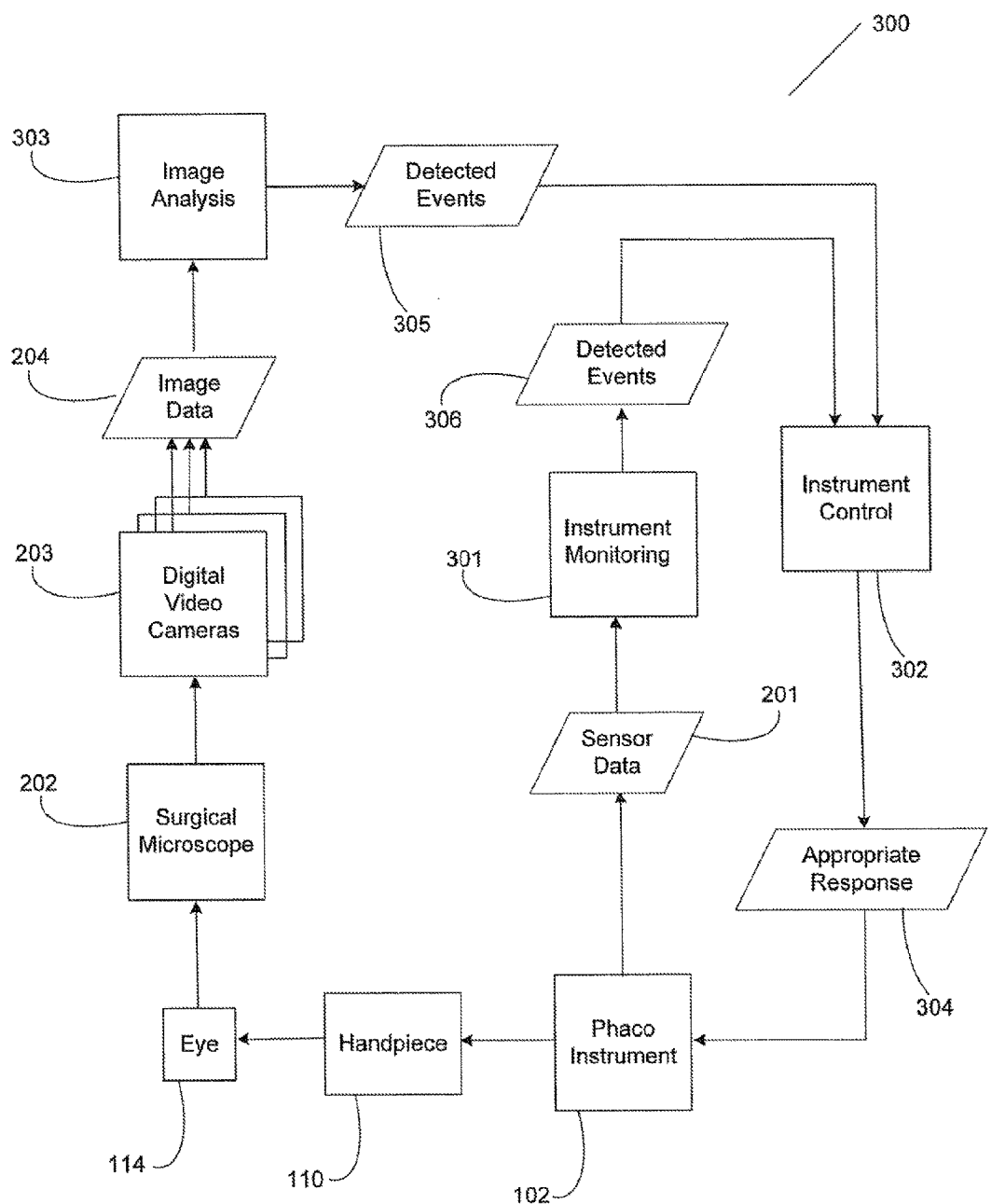
FIG. 3 is a functional block diagram illustrating components and devices for a phacoemulsification instrument control module integrated within the surgical system for real-time surgical instrument control based on detected surgical events in accordance with an aspect of the present invention.

FIG. 3 is a functional block diagram illustrating components and devices for an instrument monitor 301 module with an instrument control module 302 integrated within surgical system 200 for real-time surgical instrument control based on detected surgical events in accordance with an aspect of the present invention. From FIG. 3, a surgical microscope configured to capture an optical image of the eye requiring surgery may communicate the optical images to more than one digital video cameras 203. In this arrangement, digital video cameras 203 may convert the optical images received into video images, such as for example a digital image data stream, and provide data streams to one or more image analysis 303 modules. Image analysis 303 module may analyze the digital image data streams using 'logic' configured to detect imaging specific surgical events 305.

In conjunction with the image data streams analysis, phaco instrument monitoring 301 module may analyze data reported from multiple sensors using 'logic' configured to detect sensor reported specific surgical events 306. The present design may communicate detected surgical events 305 and 306 from the image analysis 303 module and from the phaco instrument monitoring 301 module, respectively, in real-time to phaco instrument control module 302. The phaco instrument control module arrangement may be configured to receive and process data and data analysis information realized from software programs configured to detected surgical events. The processing 'logic' may determine from this data appropriate changes to various parameters and settings for phaco instrument 102 such that implementing these changes may alter the course of the remaining surgery.

The present design may communicate changes for instrument settings and parameters from phaco instrument control 303 module to phaco instrument 102 for modifying the behavior of the surgical instrument and associated handpiece 114 in real-time. Examples of settings and parameters available for real-time modification include, but are not limited to controlling: pulse rate and waveform, rate of fluid dispensing, vacuum, aspiration, cutting speed, and combinations thereof.

During an ophthalmic surgical procedure, a surgeon may operate surgical microscope 202 to render optical images of the surgical site. The surgical microscope may include one or more digital cameras configured to convert the optical images of the surgical site into a stream of digital image data. The digital camera(s) may communicate or deliver the data stream(s) to one or more image analysis 303 modules for processing. Data processing may involve 'logic' configured to detect and report specific surgical events. For example, one image analysis software component may involve an edge detection capabilities and another image analysis software component may involve pattern recognition techniques. The present design may involve these techniques to provide information from imaging data previously not available to the surgeon.

The image analysis software may be arranged to accept input from one or more digital cameras. Multiple camera configurations may be positioned to provide for greater depth perception realized by 3D imaging techniques or positioned to provide for multiple viewing angles affording a more complete set of image data. Multiple camera configurations may be arranged to collect non-visible wavelengths such as ultra-violet and infrared and convolve this information with visible wavelength information within the optical images to form a more complete spectrum of light analysis and thus gaining access to new information available for imaging analysis.

In conjunction with operating the surgical microscope to observe the ophthalmic procedure, the surgeon may operate phacoemulsification instrument system 102 to perform activities to complete the procedure.

The present design may include one or more software programs arranged to monitor instrument sensors and to control the instrument. Referring to FIG. 3, phaco instrument monitoring 301 module may be configured to monitor each sensor incorporated in or with the phaco instrument. Phaco instrument control module 302 may be configured to provide an appropriate response 304, in real-time, sufficient for dynamically altering the operating settings and parameters of phaco-instrument 102 appropriately when specific surgical events are detected. The appropriate responses to a detected surgical event may vary depending on the nature and type of event detected. Appropriate response 304 may include but is not limited to an auditory signal emitted to alert the surgeon, adjusting an operating parameter such as vacuum or fluid flow, and shutdown of the entire system.

Phaco instrument monitoring 301 module may contain logic identifying when specific surgical events occur based upon recognition of predetermined patterns of readings from a sensor or multiple sensors.

Phaco instrument control module 302 may receive continuous and simultaneous communication of surgical events 305 originating from and detected by the image analysis and surgical events 306 originating from and detected by the instrument monitoring module. The present design may be configured to dynamically modify the phaco instrument operating settings and parameters in a predefined manner; affecting a change in the course of the remaining surgery for realizing a safer and more effective ocular procedure. The system may continuously update settings and operating parameters, in an iterative manner, to remove actively reported events. The continuous update may involve a feedback arrangement that continuously adjusts the system until the detected event is addressed or the system is shut-down. In this feedback arrangement, the present design may continue to adjust a parameter or other surgical event, reported out of range, until the event is removed by the parameter being restored to an acceptable in range value. The present arrangement may correlate surgical events detected by image analysis and instrument monitoring software for determining if they are the same event being detected and reported, or if they are unrelated events.

In another embodiment, the present design may provide information to the image analysis module for accurate imaging event detection. For example, the image analysis component logic may benefit from knowing the currently selected 'in-use' instrument operating parameters to function correctly. While depicted as multiple elements, the present designs image analysis 303, instrument monitoring 301, and instrument control module 302 software may alternatively comprise one or more distributed software modules or entities and may be realized in hardware, software, firmware, and any combinations thereof to fulfill the functionality the disclosed software programs.

Figure 4:
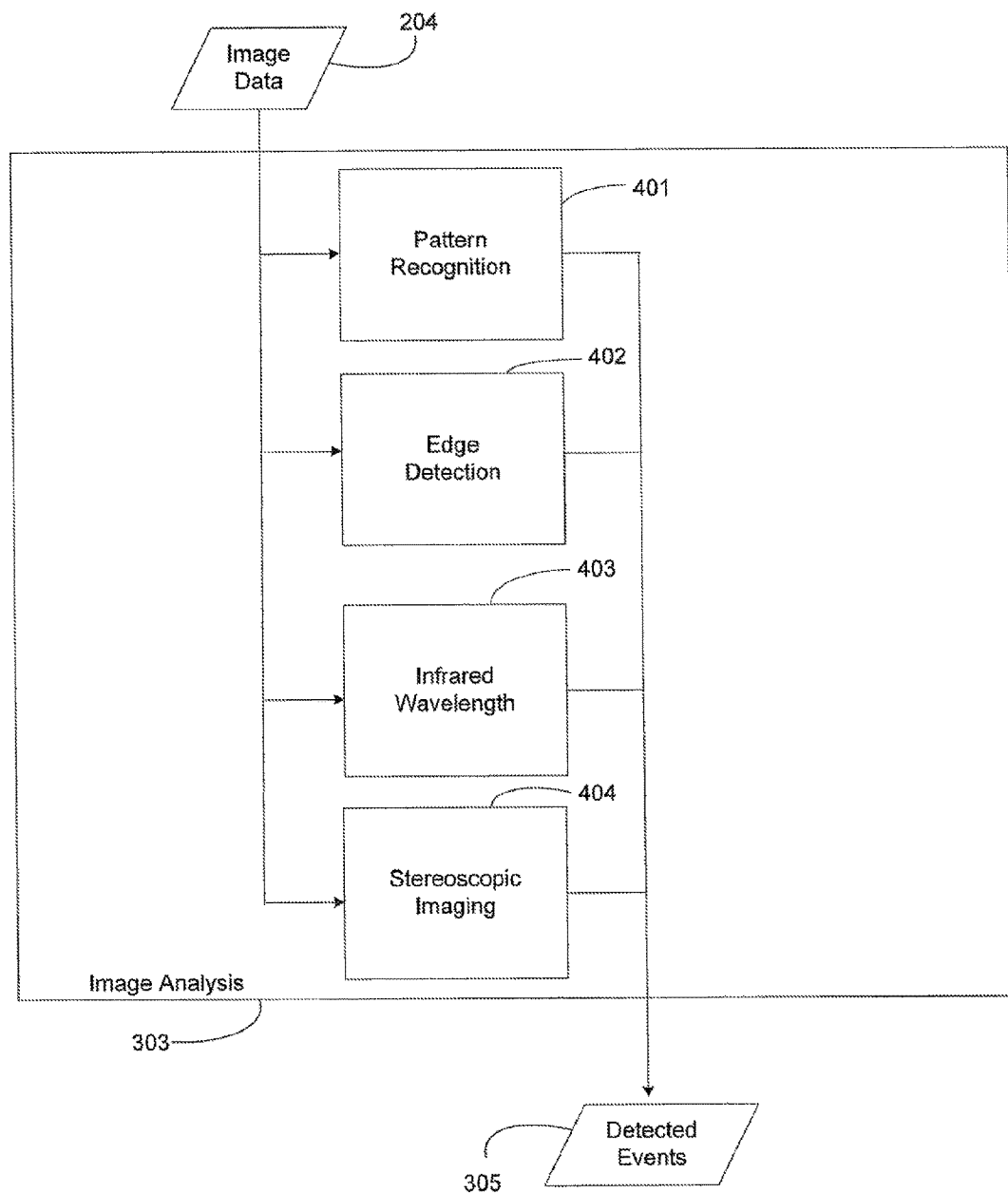
FIG. 4 is a functional block diagram illustrating components for an image analysis software module for detecting surgical events from digital imaging data in accordance with an aspect of the present invention.

FIG. 4 is a functional block diagram illustrating components for an image analysis 303 module for detecting surgical events from digital imaging data in accordance with an aspect of the present invention. Three software components are illustrated within the image analysis module. The present design may include a pattern recognition 401 component configured to analyze the image data streams for predefined data patterns. One potential pattern recognition logic design for extracting desired patterns from image data suitable for use in the current context is disclosed in "Pattern Recognition Systems and Methods", inventor Shashidhar Sathyanarayana, U.S. Patent Publication 2006/0159319, published Jul. 20, 2006, the entirety of which is incorporated herein by reference.

The present design may also include an edge detection component 402 configured to analyze the image data streams for detecting edges of one or more objects within the imaging data. One example of edge detection logic for determining the location of at least one edge of an object from image data suitable for use in the current system is disclosed in "System And Method For Edge Detection of an Image", inventor Shashidhar Sathyanarayana, U.S. Patent Publication 2004/0146201, published Jul. 29, 2004, the entirety of which is incorporated herein by reference.

The apparatus and method may include an infrared wavelength analysis component 403 for extracting information from the invisible portion of light spectrum. A stereoscopic imaging component 404 may combine edge detection, pattern recognition, ultra violet and other functionality arranged to analyze multiple data streams rendering stereoscopic content for detecting surgical events realized within multiple views of the surgical procedure. Although illustrated with three software components, image analysis module 303 may comprise additional components directed at recovering other types of information from image data 204 for the purpose of generating additional detected events at point 305. The edge detection component 402 may configure the pattern recognition and edge detection algorithms to identify one or more ocular objects of surgical interest, such as a cataract.

Figure 5:
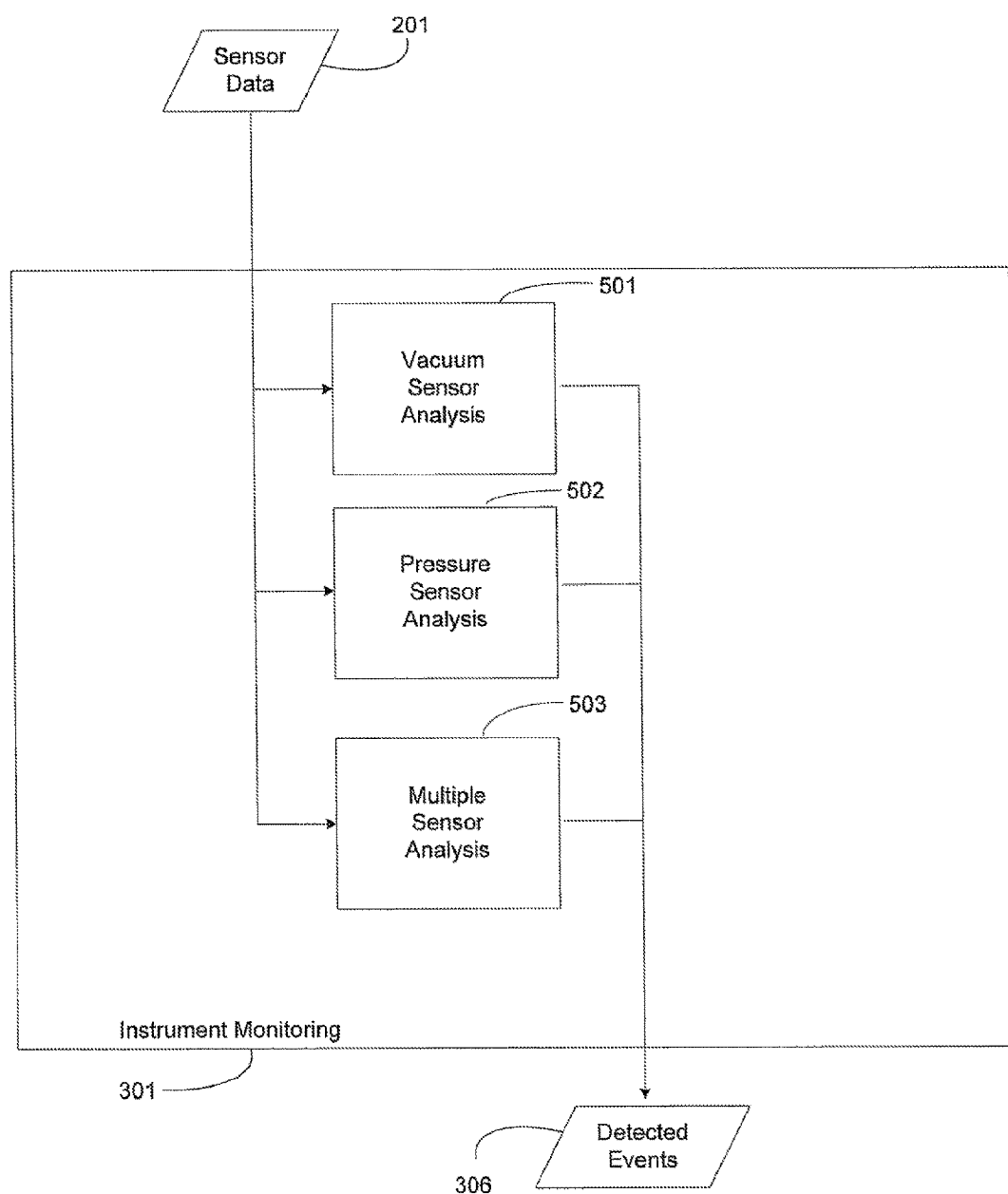
FIG. 5 is a functional block diagram illustrating components for an instrument monitoring software module for detecting surgical events from instrument sensor data in accordance with another aspect of the present invention.

FIG. 5 is a functional block diagram illustrating components for an instrument monitoring module 301 that detects surgical events from instrument sensor data. The present design may include a vacuum sensor analysis component 501 configured to analyze and monitor vacuum related information from sensor data 201. Vacuum sensor analysis component 501 may monitor sensor data 201 to determine when the actual vacuum pressure reported by the sensor is within a predetermined range of acceptable values associated with the current stage of the ocular procedure. In the situation where the actual value reported exceeds or drops below the expected predetermined range, the present design may generate detected event 306 to indicate such a change has occurred.

The present design may include a pressure sensor analysis component 502 configured to analyze and monitor pressure related information from sensor data 201. Pressure analysis 502 may monitor sensor data 201 for determining if the actual pressure reported by the sensors remains within a predetermined range of values associated with the particular stage of the ocular procedure. In the situation where the actual value reported exceeds or drops below the predetermined range, the present design may generate another detected event 306 to indicate this change in pressure.

In a similar manner, a third instrument monitoring component is illustrated at point 503 and may be configured to determine whether multiple sensors reported by the surgical instrument remain within a desired range. Although illustrated with three analysis components, instrument monitoring 301 software module may comprise additional components directed at recovering other types of information from sensor data 201 for the purpose of detecting additional events 306.

Figure 6:
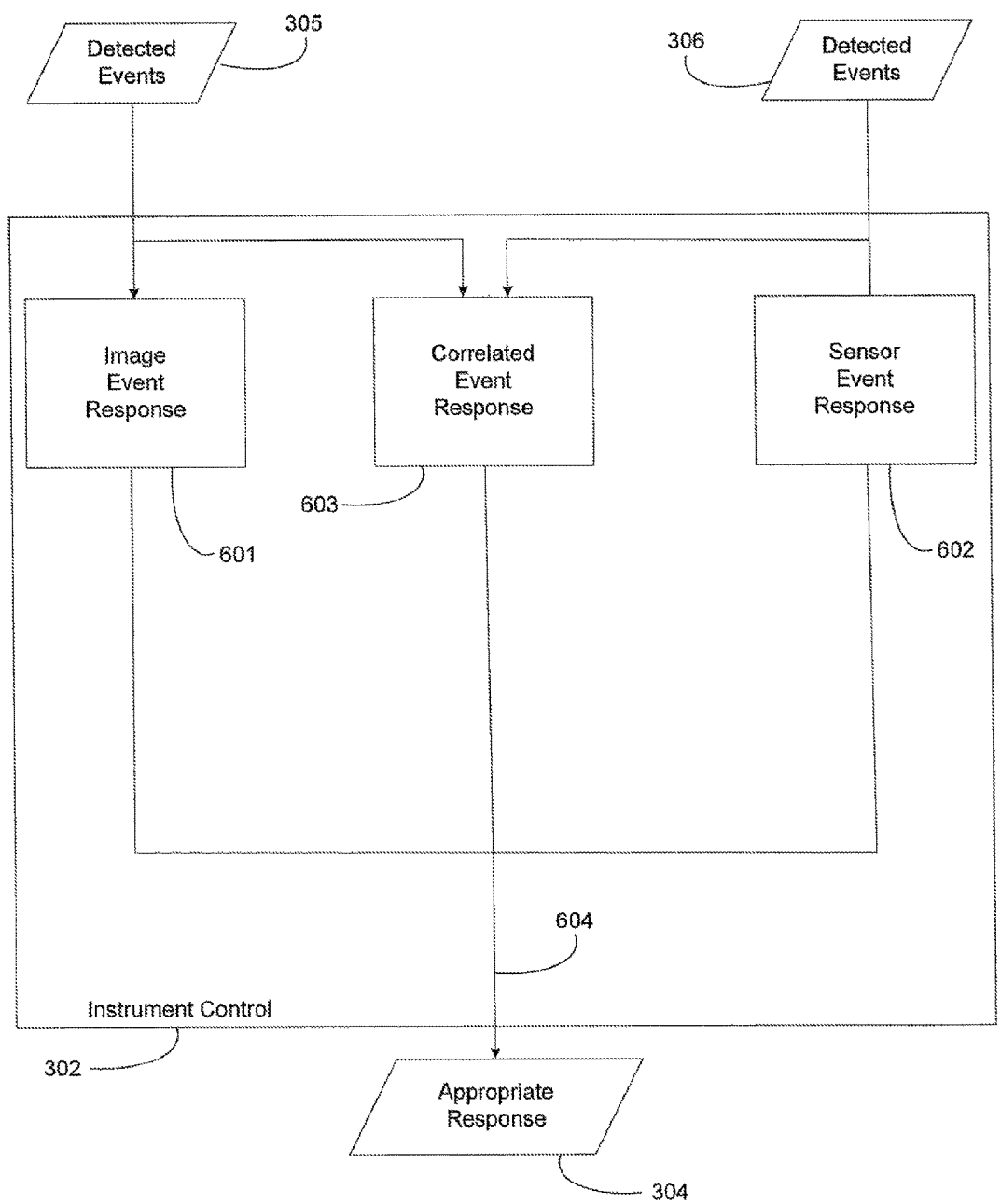
FIG. 6 is a functional block diagram illustrating components for an instrument control software module for assigning an appropriate response to detected events in accordance with another aspect of the present invention.

FIG. 6 is a functional block diagram illustrating components for an instrument control 302 module to assign an appropriate response 304 to detected events 305 and 306. The present design may include an image event response 601 component configured to receive detected events 305 from image analysis module 303 and translate each received event into an appropriate response 304. The present design may include a sensor event response component 602 configured to receive detected events 306 from the instrument monitoring module 301 and translate each received event into an appropriate response 304.

In both situations, detected event translation may involve assigning each event type a response. Each response may be converted or mapped to a predetermined set of software instructions. Instrument control module 302 may communicate commands at point 604, responsive to each detected event received, to instrument system 100 as an appropriate response 304. The communicated commands and sets of instructions may be received and executed by instrument system 100 for adjusting control of instrument host 102.

A correlated event response component 603 may be provided to receive both image and sensor detected events. Correlated event response 603 may involve comparing the received detected events for determining whether they represent the same or different surgical events. In the situation where the detected image and data event types originate from the same surgical event, the present design may assign a further appropriate response in a manner as previously described for correlated events, or may cancel any duplicate responses originating from and associated with the same surgical event.

User Interface

A user interface device executing within surgical system 200 may communicate with and enable control of the image analysis, sensor monitoring, and instrument control software for configuration and operational control of the present design's real-time surgical event detection and response automated mode. The user interface device may include, but is not limited to, a touch screen monitor, mouse, keypad, foot pedal switch, and/or a computer monitor. The system 200 typically includes algorithms, tables, and data relating desired response to detected surgical event(s). The algorithms and data may be resident within surgical system 200 or realized using external devices and/or software. Graphical user interfaces are generally known in the art, and the graphical user interface may provide, for example, touch screen or button to enable/disable automated instrument control and select from a set of operational mode(s) by the user touching the screen or pressing buttons on the interface. Other user interfaces may be provided, such as a selection device including but not limited to a foot pedal switch as discussed.

The user interface device enables the user to select system features, set system parameters, turn functionality on and off, and so forth. As noted, such a graphical user interface may be known in the art and can be engaged by touching the screen, pressing buttons, turning dials, and so forth.

Operational Use

The present design may adjust instrument settings and parameters based on stored predetermined responses assigned to the particular detected surgical event, either automatically or with user input. For example, the image pattern recognition facility may detect the presence of a cataract and determine the density of the detected cataract. The image pattern recognition facility may communicate cataract density information, in real-time, to the instrument control program. The instrument control software may assign a tailored set of instructions based on the received cataract density information and communicate the set of instructions for real-time execution by the phacoemulsification instrument affecting control of the surgical procedure in the event of a cataract having the specific density encountered. Real-time altering of instrument settings and parameters in this way may enable the surgeon to continue performing the surgical procedure efficiently, i.e. without interruption to manually adjust the instrument controls.

In another example, the image pattern recognition facility configuration may detect the presence of a capsular bag and determine the bag's condition, e.g. good, weak, or broken. The capsular bag information may be communicated from the image pattern recognition facility, in real-time, to the instrument control program. The instrument control program may be configured to assign an immediate phaco "stop-instruction" in the situation when either a weak or broken capsular bag condition is detected. In the situation where a weak or broken capsular bag is indicated, the present design may communicate the "stop-instruction" to the phacoemulsification instrument for real-time execution. Stopping the instrument in this way may prevent surgical complications and enable the surgeon to complete the procedure in a safe manner.

Further examples may include the image analysis software configured to detect a large number of similar surgical events. In this configuration, the present design may allow for assignment of a large number or pattern of similar detected events to a response, such as repeated encounters of excess pressure readings during normal operation, thus affording further refinement in the instruction sets available for controlling the surgical system.

In sum, the present design provides an ability to control parameters of a surgical instrument employed in a surgical procedure, such as an ocular surgical procedure. An image analysis module detects surgical events within an image data stream, while an instrument control module receives surgical events detected from the image analysis module and potentially other sources and generates responses to the detected surgical events. The instrument control module processes responses and transmits processed responses in the form of an instruction set. The surgical instrument receives and executes instruction sets communicated from the instrument control module during the surgical procedure.

The present design dynamically adjusts parameters applied to a surgical instrument, such as an ocular surgical instrument, detects surgical events from image data collected by a surgical microscope focused on a surgical procedure, establishes a desired response for each detected surgical event, delivers the desired response to the surgical instrument as a set of software instructions, and alters the surgical procedure based on the desired response received as the set of software instructions.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A method for dynamically adjusting parameters applied to an ocular surgical instrument, comprising:
    performing edge detection and pattern recognition analysis on image data collected by a surgical microscope in real-time to detect a first type of surgical event during an ocular surgical procedure;
    monitoring one or more input parameters and one or more operating conditions directly from one or more sensors of the ocular surgical instrument in real-time to detect a second type of surgical event during the ocular surgical procedure;
    establishing a desired response for one or more of the first type of surgical event and the second type of surgical event;
    delivering the desired response to the ocular surgical instrument as a set of software instructions; and
    altering the ongoing surgical procedure based on the desired response received as the set of software instructions.

2. The method of claim 1, wherein altering the ongoing surgical procedure comprises dynamically adjusting the one or more input parameters during the procedure.

3. The method of claim 1, wherein the performing edge detection and pattern recognition analysis identifies changed conditions during the ocular surgical procedure.

4. The method of claim 1, wherein the ocular surgical procedure comprises a phacoemulsification procedure.

5. The method of claim 1, wherein the one or more input parameters comprise vacuum pressure, power level, flow rate, and foot pedal position.

6. The method of claim 1, wherein the one or more operating conditions comprise pressure applied, pressure available, vacuum pressure, power level, flow rate, and instrument temperature.

7. The method of claim 1, further comprising:
    synchronizing a temporal relationship between the first type of surgical event and the second type of surgical event.

\* \* \* \* \*